United States Patent
Zhu et al.

(10) Patent No.: US 8,050,761 B2
(45) Date of Patent: Nov. 1, 2011

(54) METHOD FOR TREATING MYOCARDIAL INFARCTION

(75) Inventors: Qingsheng Zhu, Wexford, PA (US); Joseph M. Pastore, Woodbury, MN (US); Rodney W. Salo, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 703 days.

(21) Appl. No.: 12/150,296

(22) Filed: Apr. 25, 2008

(65) Prior Publication Data

US 2008/0208274 A1 Aug. 28, 2008

Related U.S. Application Data

(63) Continuation of application No. 11/088,231, filed on Mar. 23, 2005, now Pat. No. 7,366,567.

(51) Int. Cl.
*A61N 1/365* (2006.01)
*A61N 1/08* (2006.01)

(52) U.S. Cl. .............. 607/23; 607/9; 607/11; 607/119

(58) Field of Classification Search ............ 607/9, 11, 607/23, 119
See application file for complete search history.

(56) References Cited

U.S. PATENT DOCUMENTS

| | | | |
|---|---|---|---|
| 4,354,497 A | 10/1982 | Kahn | |
| 4,549,548 A | 10/1985 | Wittkampf et al. | |
| 4,554,922 A | 11/1985 | Prystowsky et al. | |
| 4,628,934 A | 12/1986 | Pohndorf et al. | |
| 4,674,518 A | 6/1987 | Salo | |
| 4,872,459 A | 10/1989 | Pless et al. | |
| 4,880,005 A | 11/1989 | Pless et al. | |
| 4,928,688 A | 5/1990 | Mower | |
| 5,014,698 A | 5/1991 | Cohen | |
| 5,058,605 A | 10/1991 | Slovak | |
| 5,109,842 A | 5/1992 | Adinolfi | |
| 5,156,149 A | 10/1992 | Hudrlik | |
| 5,158,079 A | 10/1992 | Adams et al. | |
| 5,174,289 A | 12/1992 | Cohen | |
| 5,233,985 A | 8/1993 | Hudrlik | |
| 5,267,560 A | 12/1993 | Cohen | |
| 5,370,665 A | 12/1994 | Hudrlik | |
| 5,514,161 A | 5/1996 | Limousin | |
| 5,534,016 A | 7/1996 | Boute | |

(Continued)

FOREIGN PATENT DOCUMENTS

EP 0522693 1/1993

(Continued)

OTHER PUBLICATIONS

"U.S. Appl. No. 10/005,184 Non Final Office Action mailed Feb. 17, 2005", 9 pgs.

(Continued)

*Primary Examiner* — Kennedy Schaetzle
*Assistant Examiner* — Natasha Patel
(74) *Attorney, Agent, or Firm* — Schwegman, Lundberg & Woessner, P.A.

(57) ABSTRACT

A method for treating patients after a myocardial infarction which includes pacing therapy is disclosed. A cardiac rhythm management device is configured to deliver pre-excitation pacing to one or more sites in proximity to an infarcted region of the ventricular myocardium. Such pacing acts to minimize the remodeling process to which the heart is especially vulnerable immediately after a myocardial infarction.

15 Claims, 3 Drawing Sheets

U.S. PATENT DOCUMENTS

| | | | |
|---|---|---|---|
| 5,584,867 | A | 12/1996 | Limousin et al. |
| 5,674,259 | A | 10/1997 | Gray |
| 5,683,429 | A | 11/1997 | Mehra |
| 5,792,203 | A | 8/1998 | Schroeppel |
| 5,797,970 | A | 8/1998 | Pouvreau |
| 5,824,019 | A | 10/1998 | Rueter et al. |
| 5,851,226 | A | 12/1998 | Skubitz et al. |
| 5,935,160 | A | 8/1999 | Auricchio et al. |
| 5,995,870 | A | 11/1999 | Cazeau et al. |
| 5,995,871 | A | 11/1999 | Knisley |
| 6,038,483 | A | 3/2000 | KenKnight et al. |
| 6,058,329 | A | 5/2000 | Salo et al. |
| 6,066,094 | A | 5/2000 | Ben-Haim |
| 6,112,117 | A | 8/2000 | KenKnight et al. |
| 6,151,524 | A | 11/2000 | Krig et al. |
| 6,152,955 | A | 11/2000 | KenKnight et al. |
| 6,223,082 | B1 | 4/2001 | Bakels et al. |
| 6,314,322 | B1 | 11/2001 | Rosenberg |
| 6,363,279 | B1 | 3/2002 | Ben-Haim et al. |
| 6,418,343 | B1 | 7/2002 | Zhang et al. |
| 6,507,756 | B1 * | 1/2003 | Heynen et al. ............ 607/9 |
| 6,556,872 | B2 | 4/2003 | Hauck |
| 6,574,506 | B2 | 6/2003 | Kramer et al. |
| 6,628,988 | B2 * | 9/2003 | Kramer et al. ............ 607/9 |
| 6,640,135 | B1 | 10/2003 | Salo et al. |
| 6,973,349 | B2 * | 12/2005 | Salo ........................... 607/11 |
| 7,096,064 | B2 | 8/2006 | Deno et al. |
| 7,206,634 | B2 | 4/2007 | Ding et al. |
| 2002/0002389 | A1 | 1/2002 | Bradley et al. |
| 2002/0082647 | A1 | 6/2002 | Alferness et al. |
| 2002/0115081 | A1 | 8/2002 | Lee et al. |
| 2003/0023278 | A1 | 1/2003 | Pastore et al. |
| 2003/0105493 | A1 | 6/2003 | Salo |
| 2003/0153952 | A1 | 8/2003 | Auricchio et al. |
| 2003/0208240 | A1 | 11/2003 | Pastore et al. |
| 2003/0233132 | A1 | 12/2003 | Pastore et al. |
| 2004/0030357 | A1 | 2/2004 | Salo et al. |
| 2004/0049236 | A1 | 3/2004 | Kramer et al. |
| 2004/0054381 | A1 | 3/2004 | Pastore et al. |
| 2004/0172079 | A1 * | 9/2004 | Chinchoy ................ 607/17 |
| 2004/0220637 | A1 | 11/2004 | Zdeblick et al. |
| 2005/0137631 | A1 | 6/2005 | Yu et al. |
| 2005/0234517 | A1 * | 10/2005 | Braunschweig et al. ..... 607/6 |
| 2006/0217773 | A1 | 9/2006 | Zhu et al. |

FOREIGN PATENT DOCUMENTS

| | | |
|---|---|---|
| WO | WO-99/10042 | 3/1999 |
| WO | WO-00/09206 | 2/2000 |
| WO | WO-01/76689 | 10/2001 |
| WO | WO-02/087694 | 11/2002 |

OTHER PUBLICATIONS

"U.S. Appl. No. 10/005,184 Non Final Office Action mailed Mar. 24, 2004", 8 pgs.

"U.S. Appl. No. 10/005,184 Notice of Allowance mailed Jul. 19, 2005", 5 pgs.

"U.S. Appl. No. 10/005,184 Notice of Allowance mailed Sep. 10, 2004", 5 pgs.

"U.S. Appl. No. 10/005,184 Response filed May 17, 2005 to Non Final Office Action mailed Feb. 17, 2005", 7 pgs.

"U.S. Appl. No. 10/005,184 Response filed Jul. 26, 2004 to Non Final Office Action mailed Mar. 24, 2004", 8 pgs.

"U.S. Appl. No. 11/088,231, Response filed Mar. 13, 2007 to Non-Final Office Action mailed Nov. 13, 2006", 9 pgs.

"U.S. Appl. No. 11/088,231, Response filed Aug. 13, 2007 to Final Office Action mailed Jun. 12, 2007", 7 pages.

"U.S. Appl. No. 11/088,231 Notice of Allowance mailed Dec. 6, 2007", 6 pgs.

"U.S. Appl. No. 11/088,231, Supplemental Notice of Allowance mailed Jan. 4, 2008", 5 pgs.

"U.S. Appl. No. 11/088,231, Supplemental Notice of Allowance mailed Feb. 20, 2008", 4 pgs.

"Final Office Action Mailed Jun. 12, 2006 in U.S. Appl. No. 11/088,231", 12 pgs.

"Non-Final Office Action Mailed Nov. 13, 2006 in U.S. Appl. No. 11/088,231", 11 pgs.

Braunwald, Nina S., et al., "Sustained Paired Electrical Stimuli; Slowing of the Ventricular Rate and Augmentation of Contractile Force", *American Journal of Cardiology*, 14, (1964), pp. 285 & 385-393.

Reiter, Michael J., et al., "Electrophysiological Effects of Acute Dilatation in the Isolated Rabbit Hear", *Circulation*, vol. 96, No. 11, (Dec. 2, 1997), 4050-4056.

Sabbah, Hani N., et al., "Delivery of Non-Excitatory Contractility-Modulation Electric Signals Improve Left Ventricular Performance in Dogs with Heart Failure", *Circulation*, Supplement 1, 100 (18), Abstract No. 631, (Nov. 2, 1999), pp. I-122.

Watanabe, Michiko, et al., "Developmental Remodeling and Shortening of Cardiac Outflow Tract Involves Myocyte Programmed Cell Death", *Development*, 125 (19), (1998), 3809-3820.

\* cited by examiner

METHOD FOR TREATING MYOCARDIAL INFARCTION

CROSS REFERENCE TO RELATED APPLICATIONS

This application is a continuation of U.S. application Ser. No. 11/088,231, filed Mar. 23, 2005, now issued as U.S. Pat. No. 7,366,567, the specification of which is herein incorporated by reference.

This application is related to U.S. Pat. No. 6,973,349, entitled "METHOD AND APPARATUS FOR MINIMIZING POST-INFARCT VENTRICULAR REMODELING", filed on Dec. 5, 2001, the disclosure of which is incorporated by reference in its entirety.

FIELD OF THE INVENTION

This invention pertains to methods of treating cardiac disease and cardiac rhythm management devices such as pacemakers and other implantable devices.

BACKGROUND

A myocardial infarction is the irreversible damage done to a segment of heart muscle by ischemia, where the myocardium is deprived of adequate oxygen and metabolite removal due to an interruption in blood supply. It is usually due to a sudden thrombotic occlusion of a coronary artery, commonly called a heart attack. If the coronary artery becomes completely occluded and there is poor collateral blood flow to the affected area, a transmural or full-wall thickness infarct can result in which much of the contractile function of the area is lost. Over a period of one to two months, the necrotic tissue heals, leaving a scar. The most extreme example of this is a ventricular aneurysm where all of the muscle fibers in the area are destroyed and replaced by fibrous scar tissue.

Even if the ventricular dysfunction as a result of the infarct is not immediately life-threatening, a common sequelae of a transmural myocardial infarction in the left ventricle is heart failure brought about by ventricular remodeling. Heart failure refers to a condition where cardiac output falls below a level adequate to meet the metabolic needs of the body which, if uncompensated, leads to rapid death. One physiological compensatory mechanism that acts to increase cardiac output is the increased diastolic filling pressure of the ventricles as an increased volume of blood is left in the lungs and venous system. This increases the preload, which is the degree to which the ventricles are stretched by the volume of blood in the ventricles at the end of diastole. An increase in preload causes an increase in stroke volume during systole, a phenomena known as the Frank-Starling principle.

Left ventricular remodeling is a physiological process in response to the hemodynamic effects of the infarct that causes changes in the shape and size of the left ventricle. Remodeling is initiated in response to a redistribution of cardiac stress and strain caused by the impairment of contractile function in the infarcted area as well as in nearby and/or interspersed viable myocardial tissue with lessened contractility due to the infarct. The remodeling process following a transmural infarction starts with an acute phase which lasts only for a few hours. The infarcted area at this stage includes tissue undergoing ischemic necrosis and is surrounded by normal myocardium. Over the next few days and months after scar tissue has formed, global remodeling and chamber enlargement occur in a third phase due to complex alterations in the architecture of the left ventricle involving both infarcted and non-infarcted areas. Remodeling is thought to be the result of a complex interplay of hemodynamic, neural, and hormonal factors.

As described above, the remodeling process begins immediately after a myocardial infarction. Until scar tissue forms, the infarcted area is particularly vulnerable to the distending forces within the ventricle and undergoes expansion over a period of hours to days as shown in a second phase of remodeling. Preventing or minimizing such post-infarct remodeling is the primary concern of the present invention.

SUMMARY

The present invention relates to a method for treating myocardial infarction which includes minimizing the ventricular remodeling that normally occurs after such an event with pacing therapy. The part of the myocardium that is most vulnerable to the post-infarct remodeling process is the infarct region, which is an area that includes sites in and around the infarct where the myocardial fibers are still intact but contractile function is impaired. The infarct region is thus the area most likely to undergo the progressive non-compensatory dilation described above with wall thinning and further impairment of function. By pacing myocardial sites in proximity to the infarct with appropriately timed pacing pulses, the infarct region is pre-excited in a manner that lessens the mechanical stress to which it is subjected, thus reducing the stimulus for remodeling.

DETAILED DESCRIPTION

Figure 1:
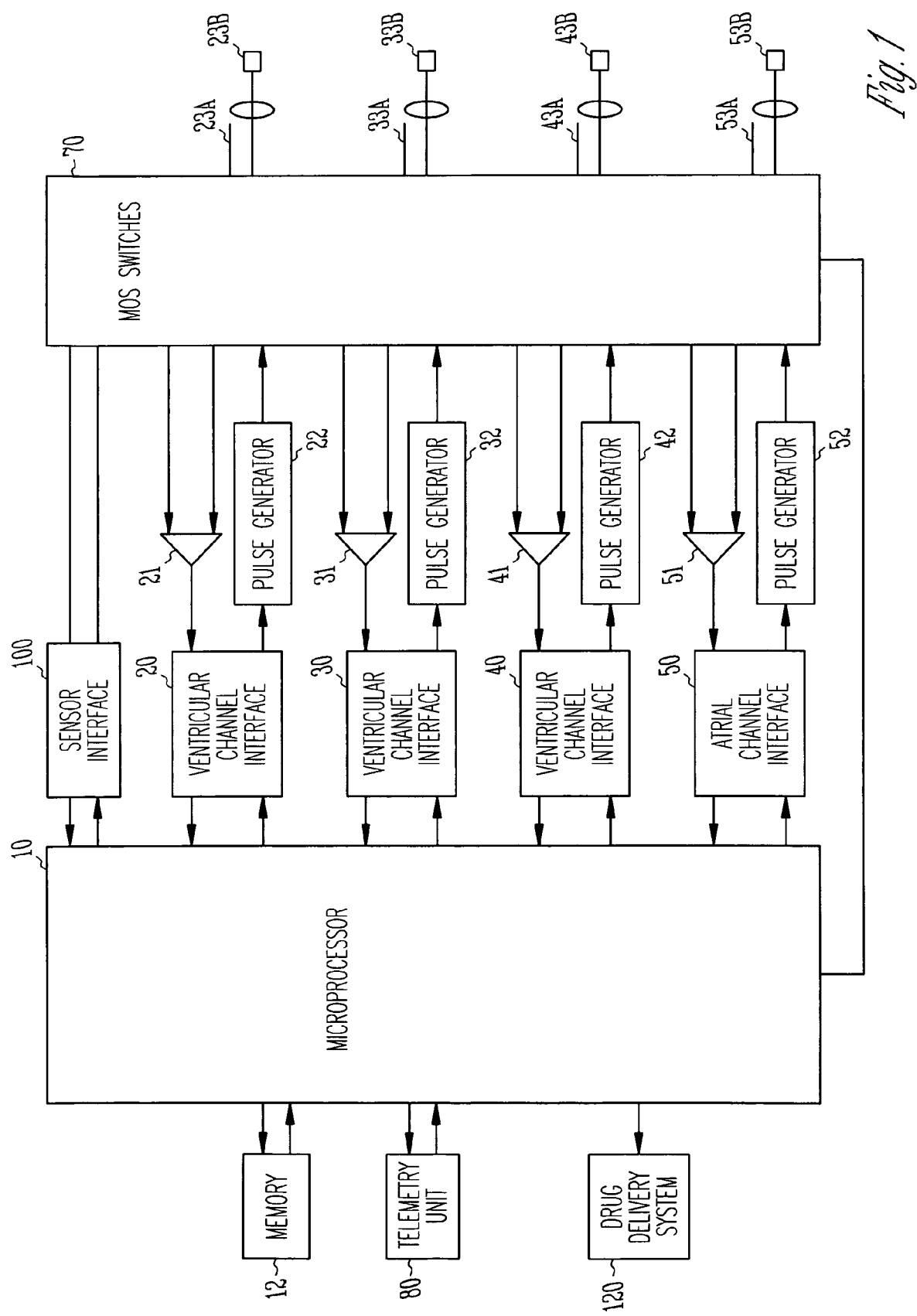
FIG. 1 is a block diagram of an exemplary cardiac rhythm management device for delivering pre-excitation pacing.

The degree to which a heart muscle fiber is stretched before it contracts is termed the preload, while the degree of tension or stress on a heart muscle fiber as it contracts is termed the afterload. The maximum tension and velocity of shortening of a muscle fiber increases with increasing preload, and the increase in contractile response of the heart with increasing preload is known as the Frank-Starling principle. When a myocardial region contracts late relative to other regions, the contraction of those other regions stretches the later contracting region and increases its preloading, thus causing an increase in the contractile force generated by the region. Conversely, a myocardial region that contracts earlier relative to other regions experiences decreased preloading and generates less contractile force. Because pressure within the ventricles rises rapidly from a diastolic to a systolic value as blood is pumped out into the aorta and pulmonary arteries, the parts of the ventricles that contract earlier during systole do so against a lower afterload than do parts of the ventricles contracting later. Thus, if a ventricular region can be made to contract earlier than parts of the ventricle, it will be subjected to both a decreased preload and afterload which decreases the mechanical stress experienced by the region relative to other regions during systolic contraction. The region will also do less work thus lessening its metabolic demands and the degree of any ischemia that may be present.

If the region around an infarct were made to contract during early systole, it would be subjected to less distending forces and less likely to undergo expansion, especially during the period immediately after a myocardial infarction. In order to cause early contraction and lessened stress, electrostimulatory pacing pulses may be delivered to one or more sites in or around the infarct in a manner that pre-excites those sites relative to the rest of the ventricle. (As the term is used herein, a pacing pulse is any electrical stimulation of the heart of sufficient energy to initiate a propagating depolarization, whether or not intended to enforce a particular heart rate.) In a normal heartbeat, the specialized His-Purkinje conduction network of the heart rapidly conducts excitatory impulses from the sino-atrial node to the atrio-ventricular node, and thence to the ventricular myocardium to result in a coordinated contraction of both ventricles. Artificial pacing with an electrode fixed into an area of the myocardium does not take advantage of the heart's normal specialized conduction system for conducting excitation throughout the ventricles because the specialized conduction system can only be entered by impulses emanating from the atrio-ventricular node. Thus the spread of excitation from a ventricular pacing site must proceed only via the much slower conducting ventricular muscle fibers, resulting in the part of the ventricular myocardium stimulated by the pacing electrode contracting well before parts of the ventricle located more distally to the electrode. This pre-excitation of a paced site relative to other sites can be used to deliberately change the distribution of wall stress experienced by the ventricle during the cardiac pumping cycle. Pre-excitation of the infarct region relative to other regions unloads the infarct region from mechanical stress by decreasing its afterload and preload, thus preventing or minimizing the remodeling that would otherwise occur. In addition, because the contractility of the infarct region is impaired, pre-excitation of the region results in a resynchronized ventricular contraction that is hemodynamically more effective. Decreasing the wall stress of the infarct region also lessens its oxygen requirements and lessens the probability of an arrhythmia arising in the region.

Pacing therapy to unload the infarct region may be implemented by pacing the ventricles at a single site in proximity to the infarct region or by pacing at multiple ventricular sites in such proximity. In the latter case, the pacing pulses may be delivered to the multiple sites simultaneously or in a defined pulse output sequence. As described below, the single-site or multiple site pacing may be performed in accordance with a bradycardia pacing algorithm such as an inhibited demand mode or a triggered mode.

1. Exemplary Implantable Device Description

A block diagram of an exemplary pacemaker for delivering pre-excitation pacing therapy to a site or sites in proximity to an infarct as described above is illustrated in FIG. 1. Pacemakers are usually implanted subcutaneously in the patient's chest and connected to sensing/pacing electrodes by leads either threaded through the vessels of the upper venous system to the heart or by leads that penetrate the chest wall. (As the term is used herein, a "pacemaker" should be taken to mean any cardiac rhythm management device with a pacing functionality regardless of any other functions it may perform.) The controller of the pacemaker is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals. A telemetry unit 80 is also provided for communicating with an external programmer or, as described below, with a system for applying counterpulsation therapy.

The device illustrated in FIG. 1 has multiple sensing and pacing channels and is therefore capable of delivering single-site or multiple site ventricular pacing. The multiple sensing and pacing channels may be configured as either atrial or ventricular channels allowing the device to deliver such pacing with or without atrial tracking. Shown in FIG. 1 is a configuration with one atrial sensing/pacing channel and three ventricular sensing/pacing channels. The atrial sensing/pacing channel comprises ring electrode 53*a*, tip electrode 53*b*, sense amplifier 51, pulse generator 52, and an atrial channel interface 50 which communicates bidirectionally with a port of microprocessor 10. The three ventricular sensing/pacing channels that include ring electrodes 23*a*, 33*a*, and 43*a*, tip electrodes 23*b*, 33*b*, and 43*b*, sense amplifiers 21, 31, and 41, pulse generators 22, 32, and 42, and ventricular channel interfaces 20, 30, and 40. A pacing channel is made up of the pulse generator connected to the electrode while a sensing channel is made up of the sense amplifier connected to the electrode. The channel interfaces include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In certain patients, pacing of sites in proximity to an infarct or within ischemic regions may be less excitable than normal and require an increased pacing energy in order to achieve capture (i.e., initiating of a propagating action potential). For each channel, the same electrode pair can be used for both sensing and pacing. In this embodiment, bipolar leads that include two electrodes are used for outputting a pacing pulse and/or sensing intrinsic activity. Other embodiments may employ a single electrode for sensing and pacing in each channel, known as a unipolar lead. A MOS switching network 70 controlled by the microprocessor is used to switch the electrodes from the input of a sense amplifier to the output of a pulse generator as well as configure sensing or pacing channels with the available electrodes.

The controller controls the overall operation of the device in accordance with programmed instructions stored in memory. The controller interprets electrogram signals from the sensing channels and controls the delivery of paces in accordance with a pacing mode. The sensing circuitry of the pacemaker generates atrial and ventricular electrogram signals from the voltages sensed by the electrodes of a particular channel. When an electrogram signal in an atrial or sensing channel exceeds a specified threshold, the controller detects an atrial or ventricular sense, respectively, which pacing algorithms may employ to trigger or inhibit pacing.

In the case where the pre-excitation pacing of the ventricle is delivered at multiple sites, the sites may be paced simultaneously or in accordance with a particular pulse output sequence that specifies the order in which the sites are to be paced during a single beat. As aforesaid, one of the benefits of pre-excitation pacing of the infarct region may be resynchronization of the contraction that results in hemodynamic improvement. An alternative mechanism is that pacing unloads the peri-infarct and infarct region while minimally compromising hemodynamic function. In either case, the therapy may be more successful if multiple ventricular sites are paced in a specified sequence such that certain of the pacing sites are pre-excited earlier than others during a single beat. Pre-excitation pacing may involve biventricular pacing with the paces to right and left ventricles delivered either simultaneously or sequentially, with the interval between the paces termed the biventricular offset (BVO) interval (also sometimes referred to as the LV offset (LVO) interval or VV delay). The offset interval may be zero in order to pace both ventricles simultaneously, or non-zero in order to pace the left and right ventricles sequentially. As the term is used herein, a negative BVO refers to pacing the left ventricle before the right, while a positive BVO refers to pacing the right ventricle first.

Cardiac resynchronization or pre-excitation therapy is most conveniently delivered in conjunction with a bradycardia pacing mode. Bradycardia pacing modes refer to pacing algorithms used to pace the atria and/or ventricles in a manner that enforces a certain minimum heart rate. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. For example, a ventricular escape interval for pacing the ventricles can be defined between ventricular events, referred to as the cardiac cycle (CC) interval with its inverse being the lower rate limit or LRL. The CC interval is restarted with each ventricular sense or pace. In atrial tracking and AV sequential pacing modes, another ventricular escape interval is defined between atrial and ventricular events, referred to as the AV delay (AVD) interval, where a ventricular pacing pulse is delivered upon expiration of the AV delay interval if no ventricular sense occurs before. In an atrial tracking mode, the atrio-ventricular pacing delay interval is triggered by an atrial sense and stopped by a ventricular sense or pace. An atrial escape interval can also be defined for pacing the atria either alone or in addition to pacing the ventricles. In an AV sequential pacing mode, the atrio-ventricular delay interval is triggered by an atrial pace and stopped by a ventricular sense or pace. Atrial tracking and AV sequential pacing are commonly combined so that an AVD interval starts with either an atrial pace or sense. As the term is used herein for biventricular pacing, the AVD interval refers to the interval between an atrial event (i.e., a pace or sense in one of the atria, usually the right atrium) and the first ventricular pace which pre-excites one of the ventricles, and the pacing instant for the non-pre-excited ventricle is specified by the BVO interval so that it is paced at an interval AVD+BVO after the atrial event. With either biventricular or left ventricle-only pacing, the AVD interval may be the same or different depending upon whether it is initiated by an atrial sense or pace (i.e., in atrial tracking and AV sequential pacing modes, respectively). A common way of implementing biventricular pacing or left ventricle-only pacing is to base the timing upon only right ventricular activity so that ventricular escape intervals are reset or stopped by right ventricular senses.

It was noted above that another benefit of pre-exciting ventricular tissue during systole is a reduction in its oxygen requirements, thus preventing or alleviating ischemia in the infarct region. Pre-excitation pacing as described above may also be employed to unload ischemic regions in either the atria or ventricles that are not associated with an infarct, which may act to prevent the development of angina in the patient or a subsequent infarct. Ischemic regions, whether or not associated with an infarct, can be identified with an angiogram, thallium scan or an MRI perfusion scan, and sites within ischemic regions so identified can be selected as pacing sites.

A device for delivering pre-excitation pacing therapy as described above may also have other functionality that can be of benefit to patients with ischemic heart disease, such as cardioversion/defibrillation. Drug delivery capability incorporated into the device may also be useful. FIG. 1 shows a drug delivery system 120 interfaced to the microprocessor which may take various forms. For example, to improve the efficacy of the pre-excitation therapy in preventing or minimizing remodeling, it may be desirable to simultaneously treat the patient with ACE (angiotensin converting enzyme) inhibitors or beta-blockers. It may also be useful to deliver biological agents such as growth factors or anti-apoptotic factors directly to the infarct region. Such delivery may be implemented by infusing the agent through a lumen in a pacing lead that is disposed near the infarct.

2. Electrode Placement

Figure 2:
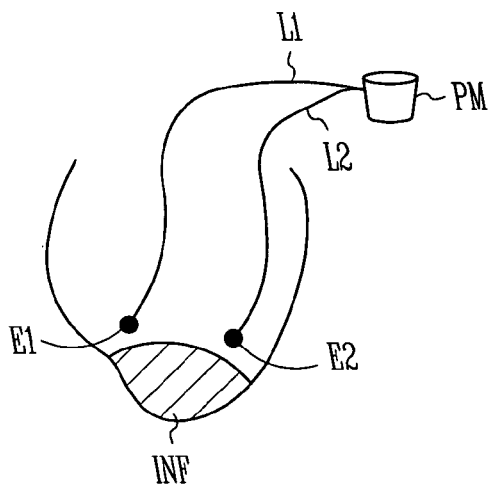
FIG. 2 illustrates a pacemaker and an exemplary pacing configuration.
Figure 3:
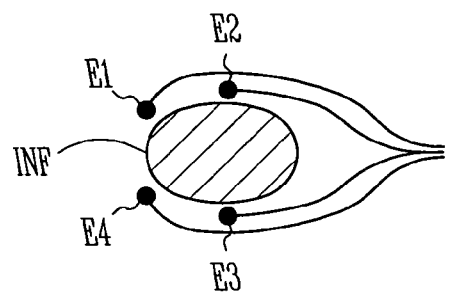
FIG. 3 illustrates a multi-site electrode arrangement.
Figure 4A:
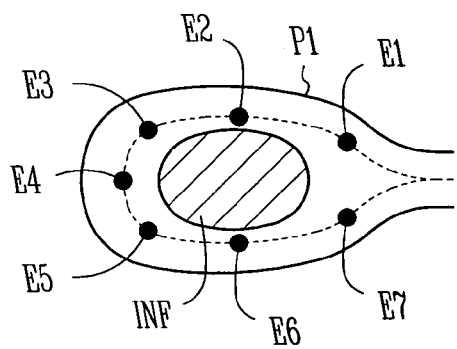
FIGS. 4A through 4C illustrate examples of patch electrodes for multi-site pacing.
Figure 4B:
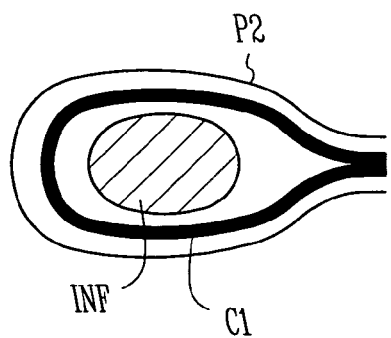
Figure 4C:
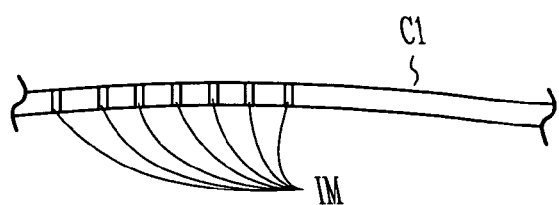

In order to place one or more pacing electrodes in proximity to an infarcted region, the area of the infarct can be identified by a number of means, including ultrasonic imaging, PET scans, thallium scans, and MRI perfusion scans. In the case of a left ventricular infarct, epicardial leads can either be placed directly on the epicardium with a thoracotomy (an open chest surgical operation) or a thoracoscopic procedure, or leads can be threaded from the upper venous system into a cardiac vein via the coronary sinus. (See, e.g., U.S. Pat. No. 5,935,160 issued to Auricchio et al., and assigned to Cardiac Pacemakers, Inc., which is hereby incorporated by reference.) FIG. 2 is an exemplary depiction of two such leads L1 and L2 that are passed from a pacemaker PM through cardiac veins in the epicardium of the left ventricle so that the pacing electrodes E1 and E2 are disposed adjacent to the infarct region INF. Alternatively, one or more pacing electrodes could be placed directly in the infarct region. In the case of lead placement by a thoracotomy or thoracoscopic procedure, it is possible to dispose the electrodes in a manner that more precisely circumscribes or overlies the infarct region. FIG. 3 shows an example of multiple electrodes E1 through E4 placed around the infarct region INF, where the electrodes may either be connected to the pacemaker by a single lead or separate leads for each electrode. FIG. 4A shows another example of an electrode arrangement where the multiple electrodes E1 through E7 are incorporated into a patch P1 so as to surround or overlay the infarct region INF. FIG. 4B shows another example of a patch P2 in which the electrode is a single continuous conductor C1 that is designed to surround the infarct region. FIG. 4C shows an exemplary construction of the conductor C1 where areas on the outer surface of the conductor are intermittently coated with an insulating material IM so as to increase the current density at the uncoated regions when the conductor is energized. Such a higher current density may be necessary in some cases to excite a myocardial region which has been rendered less excitable by ischemia.

3. Exemplary Algorithm for Treating Acute MI

Figure 5:
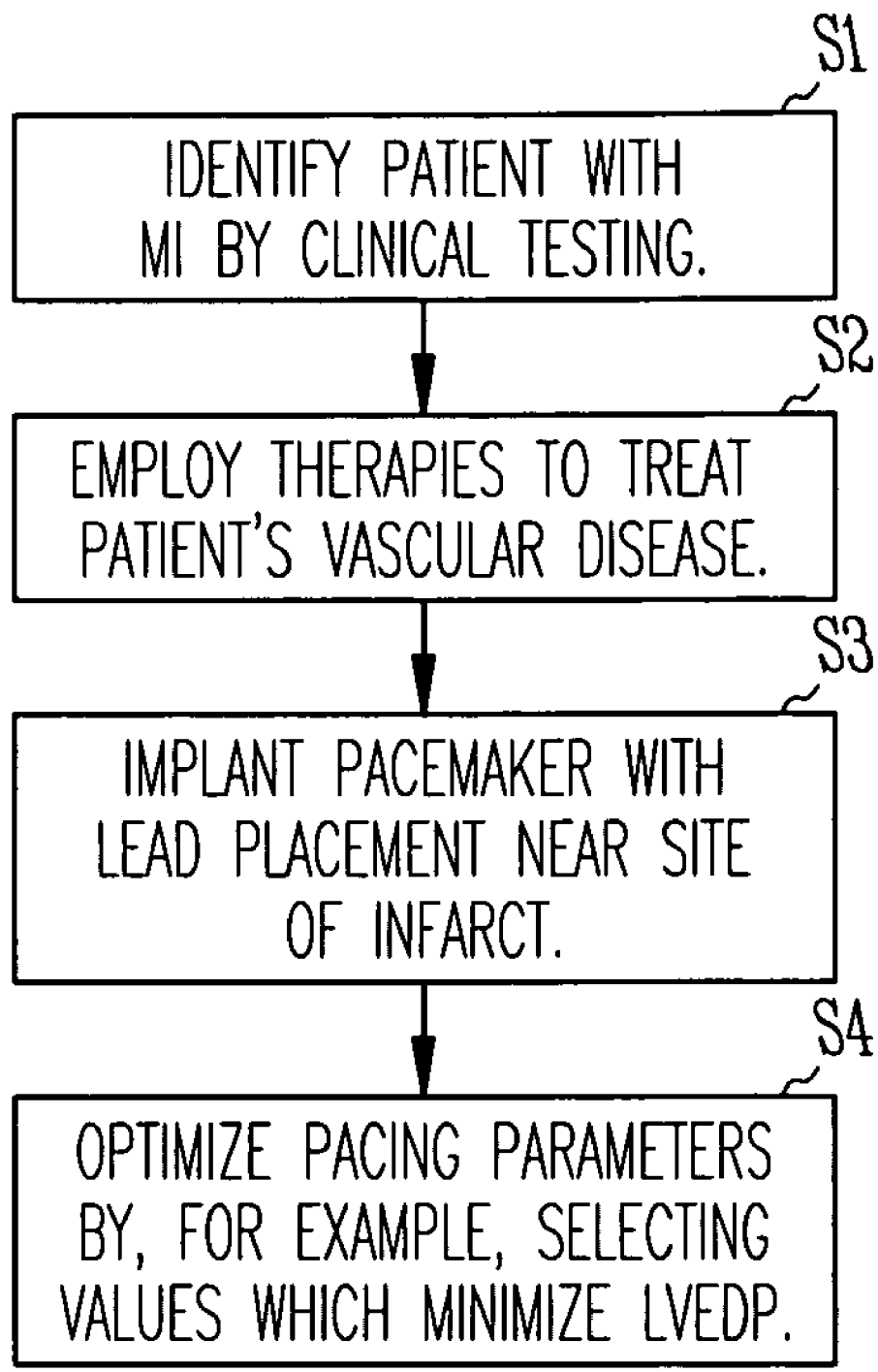
FIG. 5 is a flow chart of an exemplary treatment algorithm.

FIG. 5 illustrates an exemplary algorithm for treating a patient immediately after suffering a myocardial infarction which includes delivery of pre-excitation pacing therapy as described above. At step S1, a patient is identified as having a myocardial infarction by clinical testing such as checking for elevation of specific enzymes (e.g., troponin, creatinine kinase, creatinine kinase MB, etc.), checking for changes in electrocardiogram morphology (e.g., elevated ST segment/depression or Q wave changes), echocardiography or other imaging modalities. At step S2, various conventional therapies may be employed to treat the patient's vascular disease such as angioplasty, thrombolytics, stent placement, or bypass surgery. At step S3, the patient is implanted with a pacemaker with lead placement in or near the infarcted region as well as any other needed locations in the atria or ventricles need to implement the desired pacing mode. The pacemaker may also have defibrillation capabilities. At step S4, the pacing parameters of the selected pacing algorithm are optimized in order to maximize the myocardial wall stress around the infarcted region and/or result in optimum hemodynamics. For example, in the case of biventricular pacing, the biventricular offset interval and AV delay interval may be selected to be values resulting in a minimum left ventricular end-diastolic pressure (LVEDP). The biventricular offset interval and AV delay interval could also be selected to be those which acutely minimize LVEDP while not adversely affecting hemodynamic performance as measured by, e.g., dP/dt, pulse pressure, or left ventricular systolic pressure. In addition to or instead of the preceding criteria, the biventricular offset interval and AV delay interval could also be selected to be those which maximize synchrony between the septum and lateral wall of the heart.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A method for treating a patient with myocardial infarction, comprising:
    delivering pacing pulses to one or more sites in proximity to an infarcted area with a selected pacing mode, wherein the pacing pulses are delivered in a manner that pre-excites the site or sites in proximity to the infarcted area relative to other areas of the ventricle;
    evaluating hemodynamic performance by measuring a variable selected from dP/dt, pulse pressure, and left ventricular systolic pressure; and,
    optimizing one or more pacing parameters by selecting values which result in a minimum left ventricular end-diastolic pressure (LVEDP) without adversely affecting hemodynamic performance.

2. The method of claim 1 wherein the one or more pacing parameters that are optimized include an AV delay used in an atrial tracking or AV sequential pacing mode.

3. The method of claim 1 wherein pacing parameters are selected as values which maximize synchrony between the septum and lateral wall of the heart.

4. The method of claim 1 wherein the pacing pulses are delivered in accordance with a bradycardia pacing mode.

5. The method of claim 4 wherein the pacing mode is an inhibited demand ventricular pacing mode.

6. The method of claim 5 wherein the pacing mode is an atrial tracking mode.

7. The method of claim 1 wherein the selected pacing mode is a biventricular pacing mode.

8. The method of claim 7 wherein the optimized pacing parameters include the biventricular offset interval.

9. The method of claim 8 wherein the biventricular offset interval is selected as a value which maximizes synchrony between the septum and lateral wall of the heart.

10. The method of claim 1 wherein paces are delivered to multiple sites in proximity to the infarcted area simultaneously.

11. The method of claim 1 wherein paces are delivered to multiple sites in proximity to the infarcted area in an order defined by a specified pulse output sequence.

12. The method of claim 1 wherein the pacing pulse are delivered to multiple sites via a patch having electrodes that circumscribe a region in proximity to the infarcted area.

13. The method of claim 1 wherein the site or sites to which pacing pulses are delivered are located in the left ventricle.

14. The method of claim 1 wherein the site or sites are paced with one or more electrodes disposed in a cardiac vein.

15. The method of claim 1 wherein the pacing pulses are delivered to one or multiple sites via electrodes that are contained within the infarcted area.

* * * * *